United States Patent [19]

Neuder

[11] Patent Number: 5,625,537
[45] Date of Patent: Apr. 29, 1997

[54] CARRIER ARRANGEMENT FOR MEDICAL APPARATUS

[75] Inventor: Klaus Neuder, Obertshausen, Germany

[73] Assignee: Fresenius AG, Homburg, Germany

[21] Appl. No.: 599,113

[22] Filed: Feb. 9, 1996

Related U.S. Application Data

[63] Continuation of Ser. No. 158,074, Nov. 24, 1993, abandoned.

[30] Foreign Application Priority Data

Nov. 26, 1992 [DE] Germany .................. 42 39 625.5

[51] Int. Cl.$^6$ .................. H01R 9/16; H05K 7/12; H05K 7/14
[52] U.S. Cl. .................. 361/775; 361/741; 361/756; 361/799; 361/802; 361/803; 439/61
[58] Field of Search .................. 211/41; 248/27.1, 248/27.3; 361/733, 741, 756, 753, 775, 799, 802, 803; 439/61, 62, 73, 152, 157, 212, 213, 214, 325, 345; 307/150; 363/81

[56] References Cited

U.S. PATENT DOCUMENTS

| 3,781,567 | 12/1973 | Papsco . |
| 4,158,220 | 6/1979 | Yamamoto et al. .................. 361/775 |

FOREIGN PATENT DOCUMENTS

| 0453725A2 | 10/1991 | European Pat. Off. . |
| 0499660A1 | 8/1992 | European Pat. Off. . |
| 4030368C1 | 11/1991 | Germany . |
| 3402885A1 | 1/1993 | Germany . |

*Primary Examiner*—Donald Sparks
*Attorney, Agent, or Firm*—Whitham, Curtis, Whitham & McGinn

[57] ABSTRACT

The invention concerns a carrier arrangement (10) comprising a longitudinal column-type carrier (15), whereby a coupling arrangement is provided to establish a mechanical and simultaneously electrical connection to a medical apparatus (40). The coupling arrangement comprises two guide rails (20, 30) which are electrically insulated against each other and extend along the entire length of the carrier (15).

11 Claims, 1 Drawing Sheet

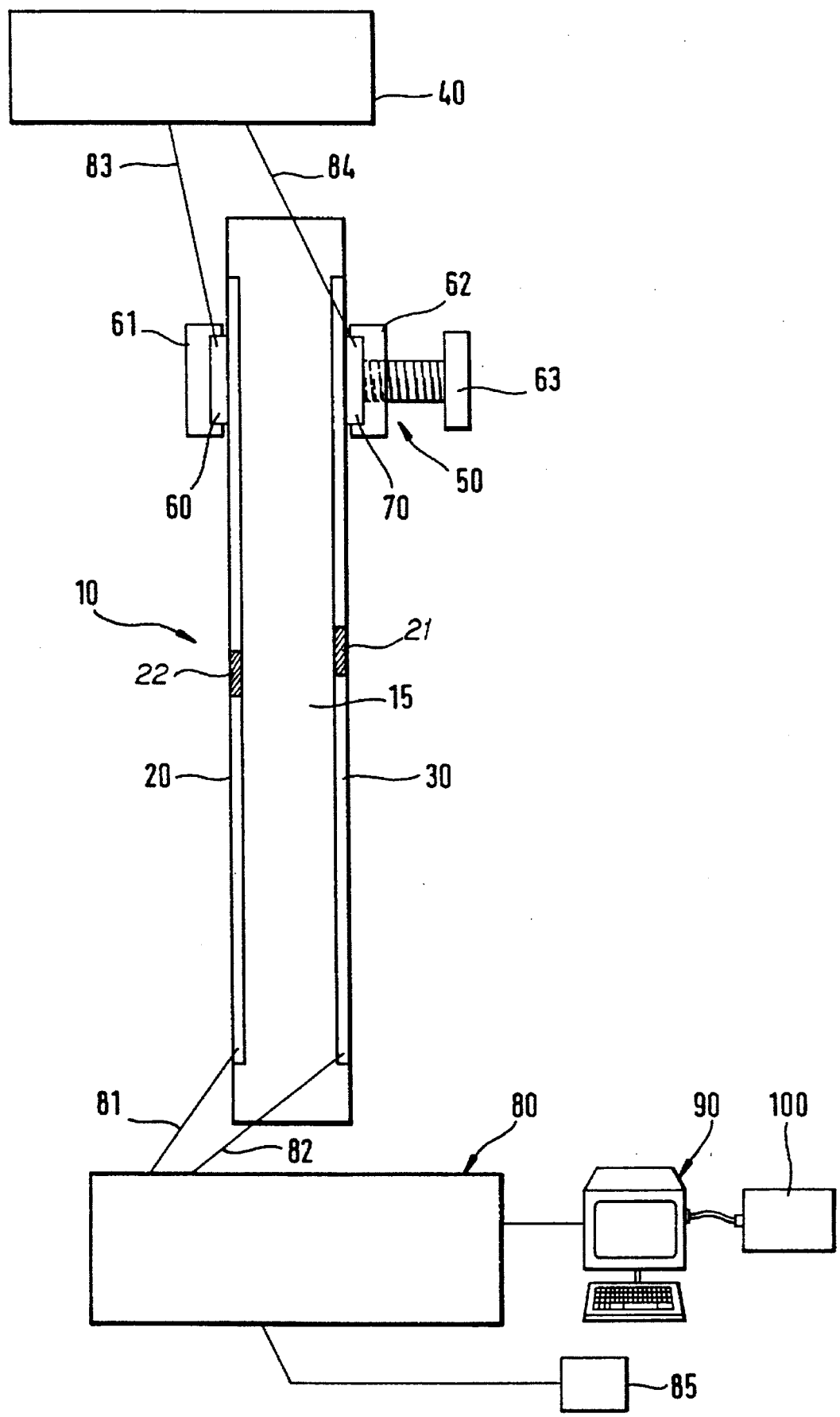

CARRIER ARRANGEMENT FOR MEDICAL APPARATUS

This is a continuation of application Ser. No. 08/158,074, filed on Nov. 24, 1993, now abandoned.

BACKGROUND OF THE INVENTION

1. Field of the Invention

The invention concerns a carrier arrangement for medical apparatus such as infusion appliances and the like.

2. Description of the Related Art

A carrier arrangement of this type is known from the DE-C-40 30 368. Medical apparatus, e.g. in the form of infusion appliances, is mounted on this generic carrier arrangement without cables. The largest area of application presently lies in the field of patient observation and infusion therapy. The carrier arrangement principally has a coupling device, whilst the medical apparatus comprises clamping means.

This known carrier arrangement comprises a column for mounting several infusion appliances, whereby the U-shaped infusion appliances are slid on the column. The column comprises ledge-shaped carrier and coupling elements. The infusion appliances to be slid on the column comprise groove-type guide and plug elements. The mechanical connection between the column and the infusion appliances is provided by the ledge-shaped carrier elements and corresponding groove-shaped guide elements in the infusion appliances. The electrical connection is established via the coupling elements and corresponding plug elements. The power supply for the infusion appliances is effected from the inside of the appliance carrier. In addition, the infusion appliances can be provided with a rechargeable accumulator when they are not mounted on the appliance carrier. This accumulator is slid onto the infusion appliance as required.

A further carrier arrangement comprising a free-standing supply column designed as an apparatus carrier is known from the DE-34 02 885. Vertical profile rails extending in pair formation on the front and rear sides of the column and with consoles, supports and ancillary parts slidable and arrestable therein by means of slide catches ere mounted on this column. These coupling arrangements establish the mechanical connection of the column and the medical apparatus. The column also comprises fluid ducts and electrical lines, so that the power supply of the medical appliances is also effected from inside the carrier arrangement, once the electrical line of the medical apparatus is connected to the corresponding supply outlet of the column.

These generic carrier arrangements, however, display the disadvantage that the mechanical and the electrical connection must be established with great precision. The electrical and mechanical connector elements can only be connected to each other after being aligned with each other. In other words, the establishment of a connection between the appliance carrier and the infusion apparatus is time-consuming. Swift employment of the generic carrier arrangements is therefore obstructed by the complicated coupling method, which is a problem in emergency situations.

SUMMARY OF THE INVENTION

The present invention thus proceeds from the problem of providing a carrier arrangement of the type specified in the preamble of claim 1, which provides greater freedom in the disposition of the medical appliances and simple, failure-proof assembly.

This problem is solved by the features of claim 1.

The coupling means of the carrier arrangement according to the invention comprise two guide rails electrically insulated against each other and extending along the entire length of the carrier. These guide rails ensure the power supply resp. data transmission as well as the mechanical attachment of at least one medical apparatus. This means that, with regard to the electrical aspect, power supply, data transmission and personnel call-up are all effected via the guide rails. This provides the advantage that there is largely no need for multiple and separate cable links, so that the preparation time required prior to employment of the medical apparatus may be substantially reduced.

The guide rails extending along the longitudinal direction facilitate infinitely variable mounting and shifting of several medical apparatus. It is a further advantage of the arrangement according to the invention that the medical apparatus may be mounted and shifted as desired in any position on the guide rails, without any need to remove the apparatus therefrom.

The subclaims contain advantageous embodiments of the invention.

In one preferred embodiment the guide rails of the carrier arrangement are formed as polished-surface metal rails. This provides the advantage that the guide rails are easier to clean and that the carrier arrangement meets hygienical requirements.

In a further preferred embodiment the guide rails of the carrier arrangement are connected to each other by coupling members, so that further interconnection of the guide rails is facilitated.

In a particularly preferred embodiment the carrier arrangement comprises a voltage and data exchange unit arranged on the base of the carrier. This results in the advantage that central control and regulation of several medical apparatus attached to the carrier arrangement is facilitated.

In a particularly preferred embodiment the voltage and data exchange unit has the form of a power supply and bus interface. This device facilitates simultaneous power supply and data transfer between the connected medical apparatus and a computer.

To facilitate control resp. data input and interactive graphical data processing, the voltage and data transfer unit may be connected to a computer or PC. The voltage/data transfer unit is also connectable to a power source or a power supply network, so that power supply is ensured.

The invention further concerns a carrier according to claim 8 constituting an independently manageable object.

The invention finally concerns a medical apparatus according to one of claims 9 to 15, preferably comprising a clamping arrangement with two electrical contacts which are contactable to the guide rails, so that the electrical connection is provided without an additional cable connection.

The clamping device advantageously comprises two clamping jaws arranged opposite each other and actuatable by means of a clamping screw or another suitable clamping means. This provides the further advantage that the electrical contact is effected simultaneously during mechanical arrest, i.e. that a mechanical connection and an electrical connection are established in one simple operation. Such a clamping device also permits easy shifting of the medical apparatus along the guide rails without any interruption to the electrical connection.

In a particularly preferred embodiment the medical apparatus comprises an integrated rechargeable accumulator, which provides the advantage that the medical apparatus continuously possesses an individually charged power source. In the case of network failure or mobile use of the medical apparatus during patient transport power supply is ensured thereby. In addition, the use of primary cells for the power supply of the infusion appliances may thus be advantageously avoided for environmental reasons.

In a further preferred embodiment the medical apparatus comprises a converter which is integrated in the clamping device. This results in the advantage that different data transmission techniques may be employed, e.g. in the case of emergency operation.

The clamping device is preferably a separate member connectable to the medical apparatus by means of a cable connection, so as to facilitate easy replacement of the clamping device, e.g. after failure. The clamping device my also be provided as an integral part of the medical apparatus.

BRIEF DESCRIPTION OF THE DRAWING

The sole FIGURE shows a schematic presentation of a carrier arrangement 10 according to the invention.

Further details, features and advantages of the invention are disclosed in the following description drawing.

The sole FIGURE shows a schematic presentation of a carrier arrangement 10 according to the invention. The carrier arrangement 10 comprises a longitudinal (preferably column-type) carrier 15 and at least two guide resp. power rails 20 and 30. The guide rails 20 and 30 are preferably of polished surface and easy to clean. The guide rails through which the power and data supply is effected are electrically insulated against each other. The guide rails 20 and 30 may be connected to each other by coupling elements 22 and 21, respectively.

DESCRIPTION OF THE PREFERRED EMBODIMENTS

In addition, a medical apparatus 40 is attached to the carrier arrangement. Several medical apparatus may, however, also be attached in series on the carrier arrangement.

The medical apparatus 40, for example, comprises a separate clamping device or fastening clamp or holder 50 connected to the medical apparatus via lines 83 and 84. The clamping device can be fastened to the carrier arrangement 10 in infinitely variable position by means of two clamping jaws 61 end 62 arranged opposite to each other. The medical apparatus 40 can thus be easily displaced along the guide rails 20, 30 of the carrier arrangement 10.

To establish the mechanical and the electrical connection along guide rails 20 and 30, the clamping device comprises electrical contacts 60 and 70. By means of clamping screw 63, the clamping jaws and the corresponding electrical contacts are clamped to the guide rails 20, 30 of the carrier arrangement. The fastening clamp may also comprise a converter of the type RS-232-CAMUS to the "bus protocol" not shown in the drawing to ensure that serial connection facilitates independent operation of the individual medical appliances connected.

Short connecting cables not shown in the drawing establish the electrical connection between the medical apparatus 40 and the converters. The power supply and the electronics for data processing (special IDK) are located in a voltage and data transfer unit 80, e.g. in the lower part of the carrier 15. From there, connections 81 and 82 to computer 90 and 85 for power supply are provided. To facilitate observation of the operation of the medical apparatus 40, an operation module 100 is linked to the computer 90.

I claim:

1. Medical device carrier arrangement for mechanically supporting medical devices comprising:

a longitudinal carrier having at least two bus contact rails electrically insulated from each other, said bus contact rails extending along an entire length of said carrier;

at least one medical device;

coupling means for releasably connecting said medical device to any location along the entire length of said bus contact rails of said longitudinal carrier, for supplying power to the medical device and for transmitting data to and from said medical device; and a voltage and data transfer unit, connected to the bus contract rails and to at least one computer system and power supply, to supply all said at least one medical device with individual data and power supply along said bus contact rails.

2. Carrier arrangement according to claim 1, wherein the bus contact rails comprise metal rails.

3. Carrier arrangement according to claim 1, wherein the bus contact rails include a polished surface.

4. Carrier arrangement according to claim 1, wherein the bus contact rails are connected to each other by coupling elements.

5. Carrier arrangement according to claim 1, wherein the voltage and data transfer device comprises a power supply and bus interface.

6. Carrier arrangement according to claim 1, wherein said coupling means further comprises a mechanically infinitely displaceable and electrically conductive clamping device.

7. Carrier arrangement according to claim 6, wherein the clamping device comprises two electrical contacts for contacting said bus contact rails.

8. Carrier arrangement according to claim 6, wherein the clamping device comprises two clamping jaws opposing each other, said clamping jaws being actuated by a clamping screw.

9. Carrier arrangement according to claim 6, further comprising an integrated power source.

10. Carrier arrangement according to claim 6, wherein the clamping device comprises a separate member for connecting to the medical device by a cable connection.

11. Carrier arrangement according to claim 6, wherein the clamping device is integral with the medical device.

* * * * *